United States Patent
Las Navas Garcia

(10) Patent No.: US 7,172,729 B2
(45) Date of Patent: Feb. 6, 2007

(54) MIXED SAMPLE MOISTURE OR ASH ANALYZER

(76) Inventor: Jose Maria Las Navas Garcia, Parque Infantas, chalet 150, Valdemorillo Madrid (ES)

( * ) Notice: Subject to any disclaimer, the term of this patent is extended or adjusted under 35 U.S.C. 154(b) by 431 days.

(21) Appl. No.: 10/378,800

(22) Filed: Mar. 4, 2003

(65) Prior Publication Data

US 2004/0175295 A1    Sep. 9, 2004

(51) Int. Cl.
    *G01N 31/12* (2006.01)
(52) U.S. Cl. ........................................................ 422/78
(58) Field of Classification Search ................... 422/78, 422/63; 436/174; 34/321, 545, 499, 500
    See application file for complete search history.

(56) References Cited

U.S. PATENT DOCUMENTS

| | | | |
|---|---|---|---|
| 4,238,450 A | 12/1980 | Bredeweg et al. | |
| 4,294,126 A | 10/1981 | Tomoff et al. | |
| 4,303,615 A | 12/1981 | Jarmell et al. | |
| 4,522,788 A * | 6/1985 | Sitek et al. ................... | 422/78 |
| 4,539,645 A | 9/1985 | Krottinger et al. | |
| 4,639,179 A | 1/1987 | Soulard | |
| 4,721,549 A | 1/1988 | Bogenschutz et al. | |
| 4,952,108 A | 8/1990 | Weigand et al. | |
| 5,064,009 A | 11/1991 | Melcher et al. | |
| 5,215,377 A | 6/1993 | Sugano | |
| 5,306,087 A * | 4/1994 | Nakamura et al. ............ | 374/14 |
| 5,341,854 A | 8/1994 | Zezulka et al. | |
| 5,382,884 A | 1/1995 | Hussami | |
| 5,385,307 A * | 1/1995 | Azar ........................... | 241/41 |
| 5,395,586 A | 3/1995 | Hemzy et al. | |
| 5,398,556 A * | 3/1995 | Lang ........................ | 73/863.11 |
| 5,906,857 A | 5/1999 | McKee et al. | |
| 6,015,532 A | 1/2000 | Clements et al. | |
| 6,117,391 A | 9/2000 | Mootz et al. | |
| 6,214,292 B1 | 4/2001 | Las Navas Garcia | |
| 2003/0003016 A1 | 1/2003 | Las Navas Garcia | |

* cited by examiner

*Primary Examiner*—Jill Warden
*Assistant Examiner*—Natalia Levkovich
(74) *Attorney, Agent, or Firm*—Robet L. Epstein; Epstein Drangel Bazerman & James, LLP

(57) ABSTRACT

An analyzer for moisture or ash testing where a robotic arm retrieves a crucible and sample from a conveyor, inserts it into a small opening in the upper surface of the furnace chamber and deposits it in an aperture on a carousel located within the furnace chamber. The carousel in the furnace chamber manipulates the crucibles within the furnace chamber. The opening in the upper surface of the furnace chamber is positioned such that when the carousel is ready for loading or unloading, an aperture in the carousel for holding the crucibles is aligned with the opening. At appropriate points during the testing cycle, individual crucibles are automatically deposited on a weighing platform connected to an internal balance through vertical motion of the carousel. Once final weighing in the test cycle is performed, the crucible is removed through the opening on the upper surface of the furnace chamber by the same robot arm which placed it in the chamber.

11 Claims, 6 Drawing Sheets

MIXED SAMPLE MOISTURE OR ASH ANALYZER

BACKGROUND OF THE INVENTION

The present invention relates to an automatic moisture or ash analyzers and the like, and more particularly, to an apparatus and a method for loading crucibles containing samples and weighing them during such analysis in such a manner as to allow tests of different samples having different dwell times in the analyzer be performed simultaneously.

Systems for moisture or ash analysis of products such as food, coal, and cement through the use of heat are well known. The samples are placed in crucibles and the weight of the sample calculated from the weight of the empty crucible and the weight of the crucible and sample. The crucibles are in turn seated on a platter or carousel positioned within a furnace chamber. A weighing platform is positioned within the furnace chamber. The samples are subject to a heating and cooling cycle. The carousel then continuously deposits the crucibles in a predetermined sequence on the weighing platform and the weights of the crucibles monitored to analyze moisture or ash content based on weight loss during heating.

U.S. Pat. No. 4,522,788, to Sitek et al., issued on Jun. 11, 1985, is directed to such a system. In this patent, the furnace chamber is opened and a number of crucibles are manually placed on a carousel for the analysis. The crucibles are weighted empty using an internal balance, the samples are then added to the crucibles and weighted. The crucibles and samples are heated in nitrogen atmosphere to remove moisture, after moisture is obtained the furnace lid partially opens to install covers manually on top of crucibles, covers are weighed, furnace lid closes and heats up to obtain volatiles. The crucible samples and covers are cooled down to approximately 600° C., the furnace lid opens partially and covers are removed manually in the presence of nitrogen atmosphere. The lid closes and the furnace is heated in oxygen atmosphere to obtain ash. The furnace chamber is cooled down to room temperature then reopened and the crucibles removed.

There is a need for a moisture or ash analysis system that can automatically insert and remove crucibles in a furnace chamber at the appropriate stages of the analysis without requiring manual intervention, cooling of the furnace chamber or opening of the furnace chamber in order to make the analyses more efficient and safer. There is also a need for a moisture or ash analysis system which is capable of analyzing simultaneously different samples having different dwell times during the test.

SUMMARY OF THE INVENTION

The present invention uses a furnace chamber which is closed through all stages of the analysis. During use the crucibles are weighed on an external balance which is connected to a recording system or computer which records the initial weight of each crucible without and with the sample. The crucibles are staged on a conveyor prior to being placed in the furnace chamber by a robotic arm. The robotic arm retrieves each crucible from the conveyor, inserts it into a small opening in the upper surface of the furnace chamber and deposits it into an aperture on a carousel located within the furnace chamber.

The carousel in the furnace chamber manipulates the loaded crucibles within the furnace chamber. The carousel rotates and move up and down along its central axis. The carousel has apertures for holding the crucibles and suspending them within the furnace chamber. The opening in the upper surface of the furnace chamber is positioned such that when the carousel comes into position for loading or unloading, an aperture in the carousel for holding the crucibles is aligned with the opening on the upper surface of the furnace chamber.

At appropriate points in the testing cycle, individual crucibles are automatically deposited on an internal balance through vertical motion of the carousel. A pneumatic cylinder acts to raise and lower the carousel so that a crucible is deposited on the weighing platform of the internal balance. The weight of each crucible is recorded and compared a number of times during the test cycle. Once the final weighing in the test cycle is performed, the crucible is removed through the opening on the upper surface of the furnace chamber by the same robot arm which placed it in the chamber.

The system may be used for both moisture or ash analysis as required. As is commonly known in the art, moisture content may be analyzed when the furnace chamber is used at lower temperatures such as 105 degrees Celsius in a nitrogen atmosphere and for ash analysis when the furnace chamber is used at higher temperatures such as 600 degree Celsius and higher in an oxygen atmosphere. Different types of samples may be simultaneously analyzed. Samples which take a longer period of time to analyze at a given temperature will remain in the furnace chamber while other samples requiring less time may be removed to allow other crucibles to be placed in the furnace chamber for analysis. Because there is no cool down required for insertion or removal of crucibles, this process is a highly efficient means of continuous operation of the test apparatus.

DETAILED DESCRIPTION OF THE INVENTION

Figure 1:
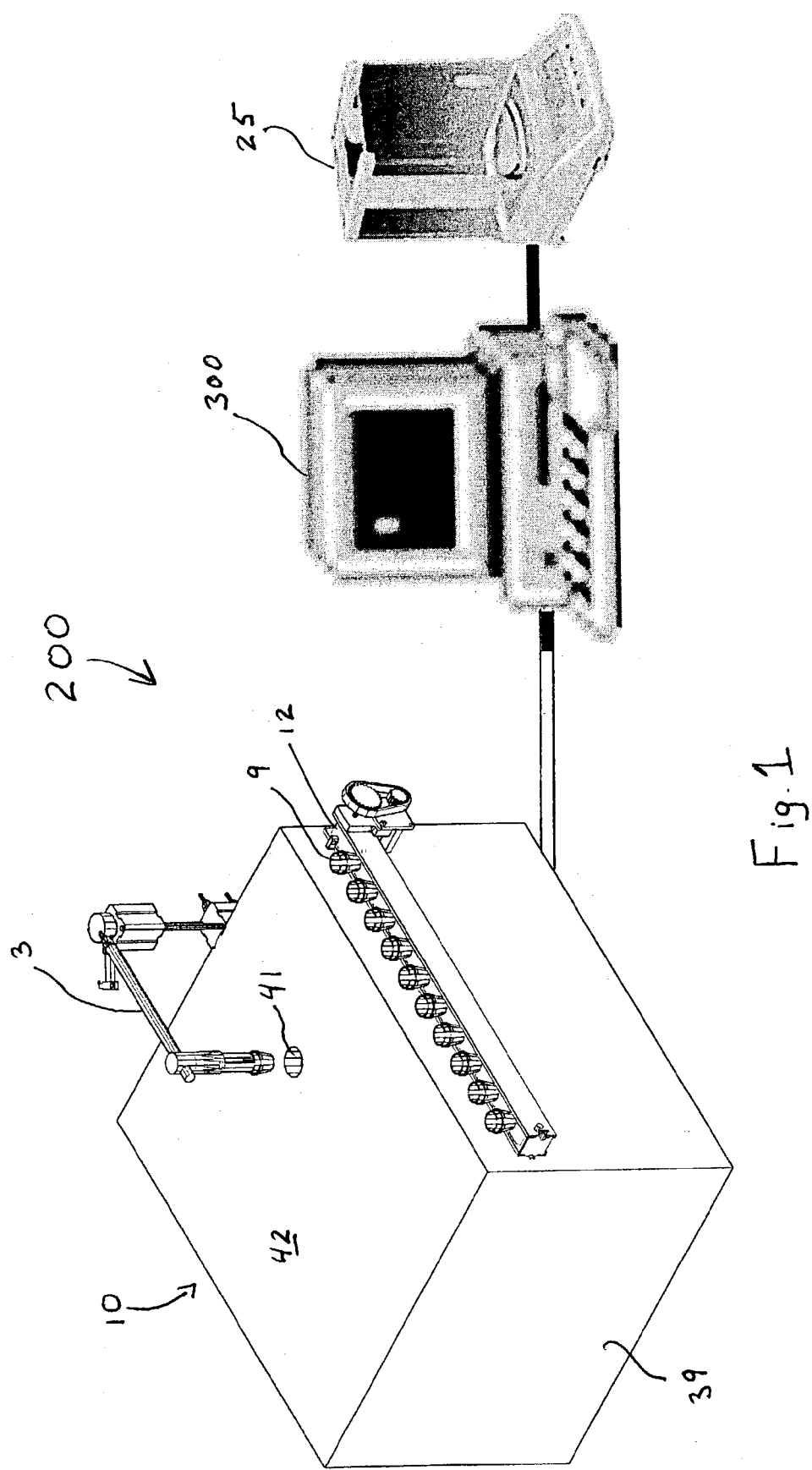
FIG. 1 is a schematic drawing showing the present invention and the relation between the furnace chamber, computer system and external balance.

FIG. 1 shows the improved moisture or ash analyzer system 200 of the present invention. The external balance 25 takes an initial reading of the weight of the crucible 9 with and without a sample just moments before the crucible 9 is inserted into the heated furnace chamber 10. Each crucible 9 with a sample is positioned on the conveyor 12 after being weighed on the external balance 25 for loading into the furnace chamber 10. The conveyor belt 12 is used for a queuing system for the crucibles 9 during the process. The conveyor is operated by a step motor connected to and controlled by the computer system 300. The crucibles 9 are placed in the furnace chamber 10 by means of robot arm 3. The robot arm 3 is controlled by the computer system 300 and capable of grasping a crucible 9 for insertion into the furnace chamber 10. Alternatively, the robot arm 3 may move the crucibles to the external balance 25 and then move the crucible 9 from the external balance 25 directly into the furnace chamber 10. The order of events will vary depending on the equipment available.

As can be seen in FIG. 1, the computer 300 is connected to the external balance 25 and an internal balance 21 is positioned to weigh crucibles 9 in the furnace chamber 10. This allows the computer 300 to record the weight of the crucible 9 with and without the sample as measured by external balance 25 and the weight as measured by the internal balance 21 at various points during the testing cycle. The data is recorded and stored and is matched for analysis. The furnace chamber 10 has an outer cover 39. The top 42 of the outer cover 39 has a hole 41 for insertion and removal of loaded crucibles 9.

Figure 2:
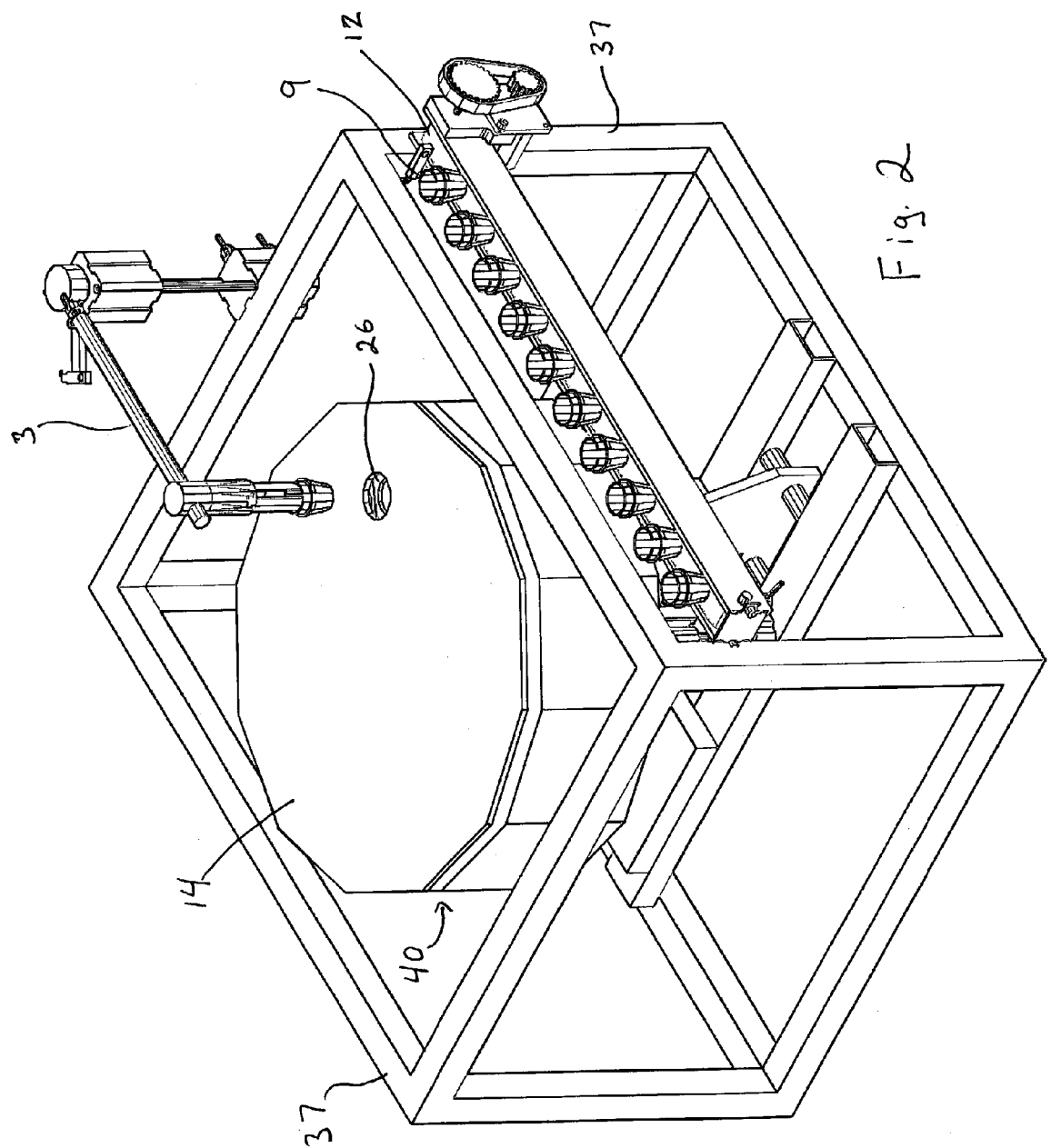
FIG. 2 is a perspective view of the furnace chamber of the present invention with the view having the external cover of the furnace chamber removed.
Figure 3:
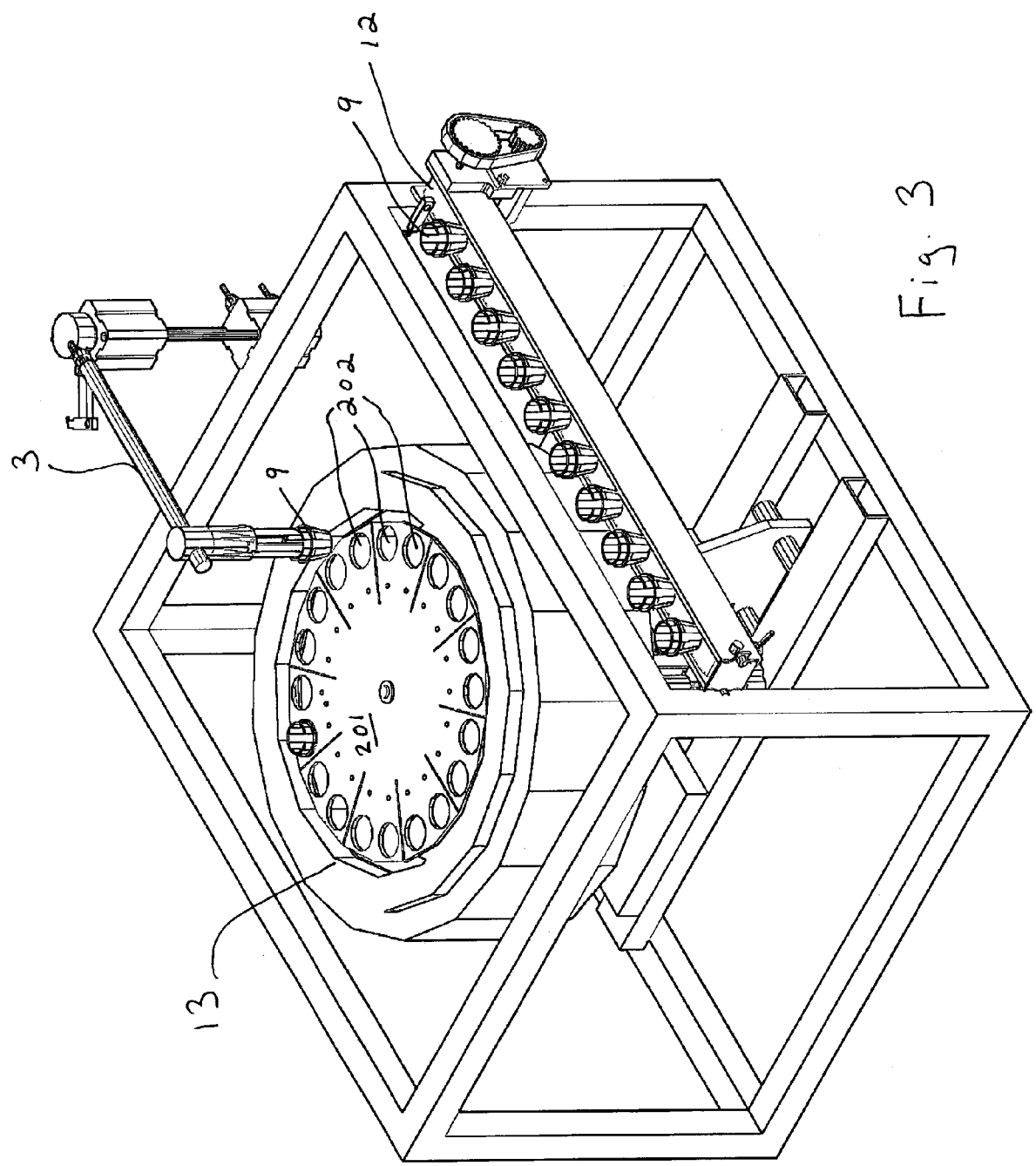
FIG. 3 is a perspective view of the furnace chamber of the present invention with the view having the refractory isolation cover removed.

FIG. 2 shows the furnace chamber 10 without the external cover 39. The conveyer belt 12 is attached to the frame 37 of the furnace chamber 10. There is an isolation cover 14 which forms the top of the refractory chamber 40 with a cover hole 26 which is aligned with hole 41 in the furnace chamber cover 39. FIG. 3 shows the furnace chamber without the refractory isolation cover 14. A carousel 201 is positioned beneath the isolation cover 14. The hole 26 in the isolation cover is positioned such that when the carousel 201 comes to a rest, an aperture 202 of the carousel 201 will be aligned with the hole 26. Once the hole 26 and an aperture 202 are aligned, the robotic arm 3 will place a crucible 9 through the hole 26 and place the crucible 9 into an aperture 202 in the carousel 201

Figure 4:
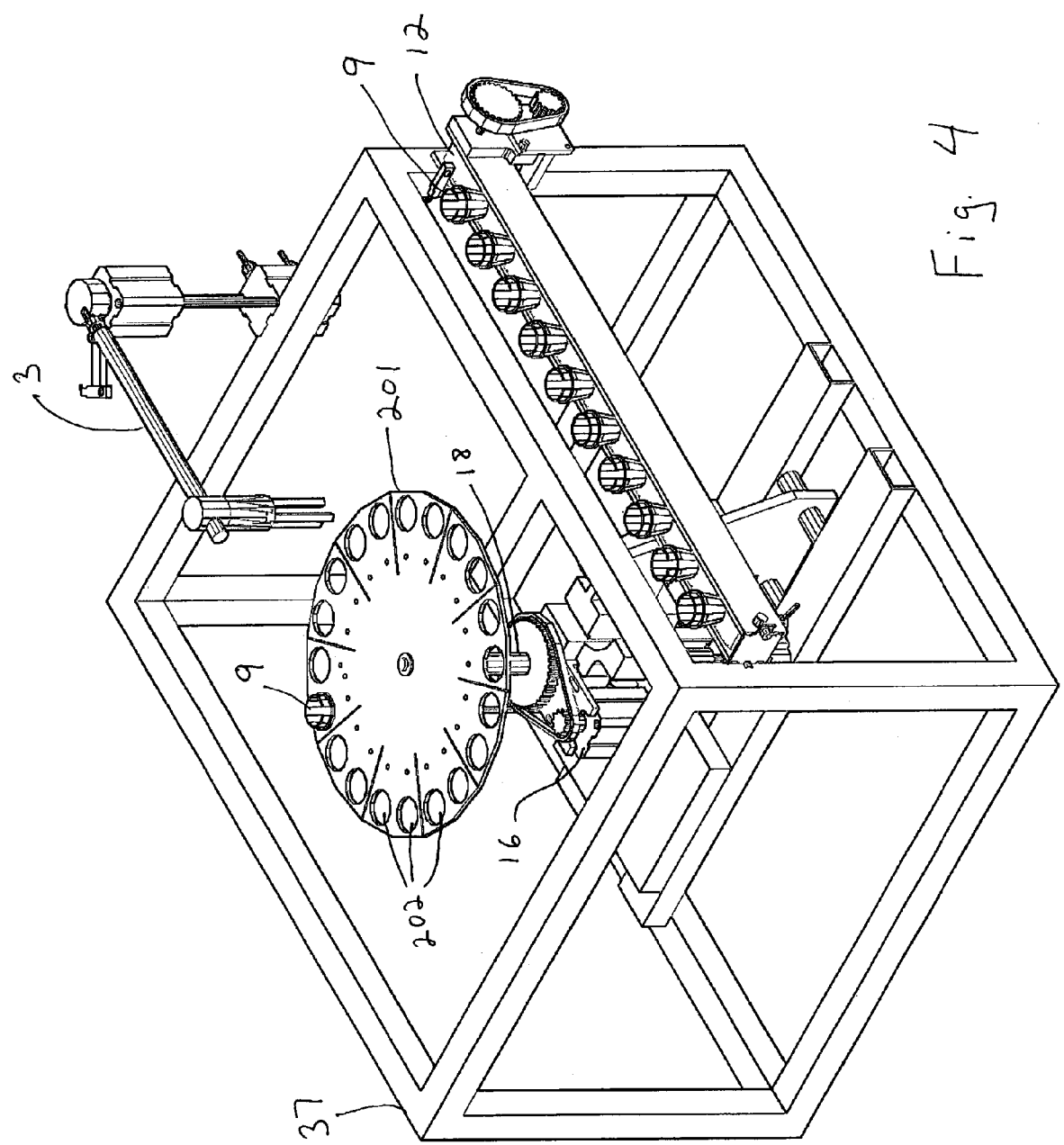
FIG. 4 is a perspective view of the furnace chamber of the present invention showing the external frame, carousel and conveyor belt.

FIG. 4 shows the carousel 201 and frame 37 of the furnace chamber 10 of the present invention without the refractory chamber 40. Once a crucible 9 is placed in the carousel 201, its position is recorded in the computer 300 and any measurements taken which relate to that crucible 9 is recorded and matched with the initially recorded data taken at the time of the weighing on the external balance 25.

The operation of the carousel 201 is best shown in FIG. 4. Once a crucible 9 is placed in an aperture 202 by robot arm 3 it revolves with the carousel 201 around the carousel's central axis. The carousel 201 is turned and rotates around its central axis by means of a motor 16 which rotates the shaft 18 of the carousel 201. The motor 16 may be directly connected to the shaft 18 or by any other conventional means such as a belt and pulley system as shown in FIG. 4.

Figure 7:
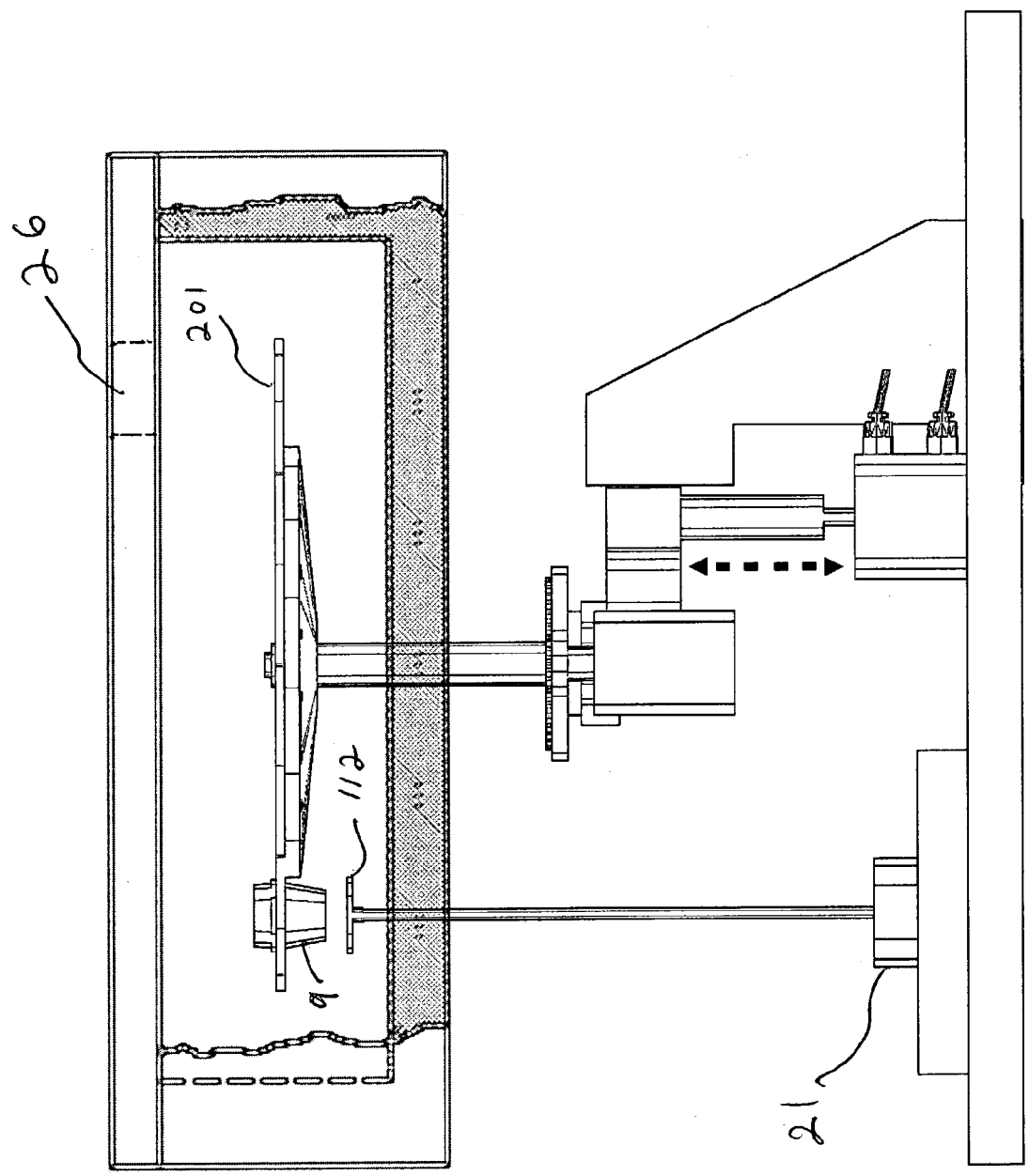
FIG. 7 is a cross sectional view of the furnace chamber of the present invention.

As seen in FIG. 7, a weighing platform 112 is positioned within the heating element 13 but the internal balance 21 is located outside of the heating element 13. At predetermined intervals, a designated crucible 9 is positioned above the weighing platform 112 and the carousel 201 stops rotating. When the carousel 201 stops rotating, the carousel 201 is lowered so that the crucible 9 is placed on weighing platform 112 and is no longer supported by the carousel 201. The vertical movement of the carousel 201 is controlled by a pneumatic cylinder via carousel shaft 18. Although pneumatic means are preferred, any other means known in the art to raise or lower a structure such as worm gears or pulley arrangements may be used to control the vertical movement of the carousel 201.

Figure 5:
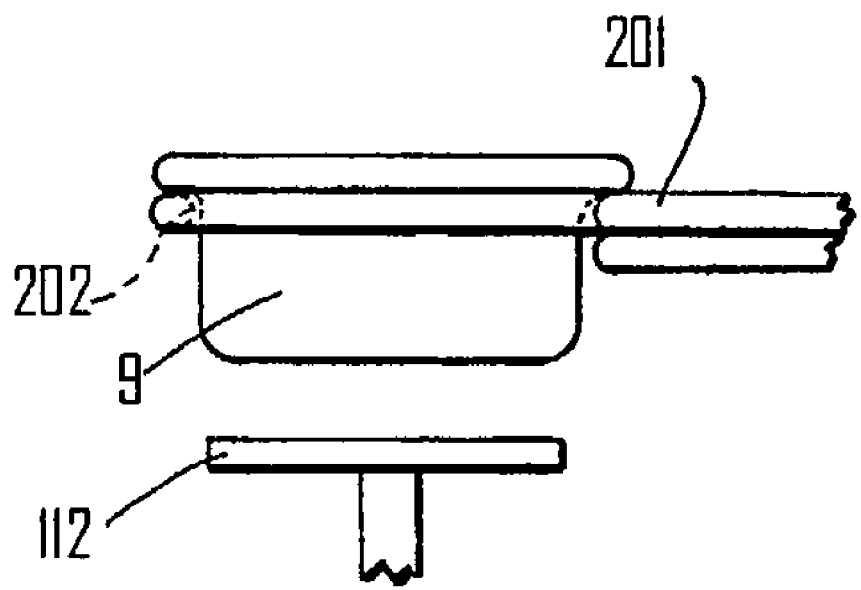
FIG. 5 is a view of a crucible positioned above the weighing platform.
Figure 6:
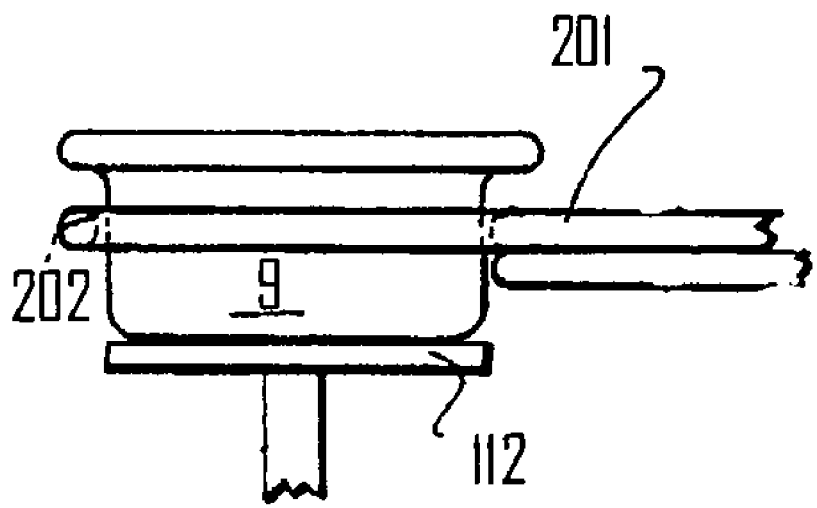
FIG. 6 is a view of the crucible positioned on the weighing platform.

FIG. 5 shows the crucible 9 positioned above the weighing platform 112 and FIG. 6 shows the release of the crucible 9 on the weighing platform 112 so the weight of the crucible 9 and sample may be recorded by the internal balance 21. The time a crucible 9 remains in the furnace chamber 10 as well as the number of weights recorded will depend on the sample and type of analysis being performed.

Once the analysis is complete, a crucible 9 may be removed by the robotic arm 3. This procedure may be performed without the furnace chamber 10 losing heat since the furnace chamber will not be required to open during loading and unloading of the crucibles 9 into the carousel 201. Given that crucibles 9 may be loaded and unloaded individually without having to lower the temperature of the furnace chamber 10, multiple types of samples with different dwell times may be analyzed simultaneously. However, is should be noted that due to differences in temperature ranges and atmospheres, if the system 200 is used for moisture analysis, then all samples within the furnace chamber 10 will be analyzed for moisture. The same holds true for samples being analyzed for ash, all samples in the furnace chamber 10 must be analyzed for the same type of analysis.

The carousel 201 itself can be made from any rigid material that can withstand elevated temperatures without substantial deterioration or distortion, preferably metallic sheet materials such as stainless steels, and any other such materials used in the art.

The advantages of the improvement of the present invention may be understood by comparison with the prior art. A proximate analysis including a cycle for moisture, volatiles and ash using the prior art analyzer of U.S. Pat. No. 4,522,788 requires the following steps: obtaining the weight of the crucibles, opening the furnace, introducing sample to all crucibles, re-weighing to obtain sample weight, closing the furnace, heating the furnace chamber, opening the furnace, reweighing to obtain moisture content, and manually covering the crucibles, closing the furnace chamber and ramping the temperature higher to obtain volatiles, cooling the furnace chamber down, opening the furnace chamber half way (to avoid too much heat loss) to allow manual removal of the crucible covers with tools in order to go to the ash cycle, opening the furnace and weighing the crucible. The opening and closing of the furnace is done manually with a resultant loss of time and heat energy.

In the system of the present invention, as the weight of each crucible and sample is obtained, the robotic arm places the crucible into the furnace chamber. The analysis cycle starts the moment the crucibles are introduced to the furnace chamber and continues without manual intervention or disruption due to other crucibles and samples. When the cycle for a particular crucible is complete, the crucible and sample are removed.

The system of the present invention provides the following advantages over the prior art: ability to analyze multiple types of samples for moisture analysis or ash analysis, reduction of time required for analysis since re-heating of the furnace chamber is not necessary; safety, no danger of an operator being burned due to manual handling of crucibles in the furnace chamber; the convenience of unattended operation; and better reproducibility of the analytical results.

It is understood that the present embodiments described above are to be considered as illustrative and not restrictive. It will be obvious to those skilled in the art to make various changes, alterations and modifications to the invention described herein. To the extent that these variations, modifications and alterations depart from the scope and spirit of the appended claims, they are intended to be encompassed therein.

I claim:

1. Apparatus for moisture or ash analysis comprising:
   a furnace comprising an enclosure with entrance means and a top surface, said top surface having a hole;
   a balance having a weighing platform positioned within said furnace enclosure;
   internal rotatable support means located within said furnace enclosure, at a level above said weighing platform, having a plurality of positions arranged in a generally horizontal circular configuration, each of said positions adapted to support a crucible, each of said crucibles holding a sample of the material to be analyzed, wherein one of said positions is aligned with said weighing platform and a different one of said positions is aligned with said hole;
   external means located outside said furnace enclosure for supporting one or more crucibles;
   automatic means for transporting crucibles between said external supporting means and said internal rotatable support means through said hole in said top surface of said furnace enclosure;
   means for rotating said internal rotatable support means;
   elevation means for vertically shifting said internal rotatable support means to deposit and remove the aligned crucibles on and off said weighing platform; and
   means for controlling said automatic means for transporting crucibles, said means for rotating said internal rotatable support means and said elevation means to transport crucibles into said furnace enclosure through said hole without having to open said furnace enclosure.

2. Apparatus according to claim 1 wherein said controlling means controls said means for rotating said internal rotatable support means and said elevation means to allow weighing of crucibles on said weighing platform while crucibles are being transported through said hole.

3. Apparatus according to claim 1 wherein said automatic means for transporting crucibles comprises robot means.

4. Apparatus according to claim 3 wherein said external means for supporting crucibles comprises external weighing means for sequential weighing of the crucibles with and without samples prior to being placed in the furnace enclosure.

5. Apparatus according to claim 4 wherein said robot means comprises a robot arm capable of taking samples from said external means for supporting crucibles after the crucibles and sample have been weighed.

6. Apparatus according to claim 4 wherein said robot means comprises a robot arm capable of lifting the crucible and sample from said external weighing means and placing it into the furnace enclosure.

7. Apparatus according to claim 1 wherein said external means for supporting crucibles comprises conveyor means.

8. Apparatus according to claim 4 wherein said controlling means further comprises computer means connected to said external weighing means and said balance, said computer recording the weight of the crucibles weighed by said external weighing means and by said balance.

9. Apparatus according to claim 8 wherein said external means for supporting crucibles comprises conveyor means and further comprising means for moving said conveyor means, said computer means being connected to said conveyor moving means to control the movement of said conveyor means.

10. Apparatus according to claim 1 further comprising computer means operably connected to control said automatic means for transporting crucibles.

11. Apparatus according to claim 1 wherein said external means for supporting crucibles comprises conveyor means and external weighing means and wherein said controlling means controls said automatic means for transporting crucibles to transfer crucibles between said external weighing means and said conveyor means.

* * * * *